United States Patent
Hirsh

(10) Patent No.: US 12,408,889 B2
(45) Date of Patent: Sep. 9, 2025

(54) NON-INVASIVE SYSTEM AND METHOD FOR DETECTING AND ACCURATELY QUANTIFYING SUBCLINICAL AND CLINICAL SYSTOLIC AND DIASTOLIC HEART FAILURE

(71) Applicant: COOPER HEALTH SYSTEM, Camden, NJ (US)

(72) Inventor: Robert Alan Hirsh, Merion Station, PA (US)

( * ) Notice: Subject to any disclaimer, the term of this patent is extended or adjusted under 35 U.S.C. 154(b) by 402 days.

(21) Appl. No.: 18/106,004

(22) Filed: Feb. 6, 2023

(65) Prior Publication Data

US 2024/0008837 A1 Jan. 11, 2024

Related U.S. Application Data

(60) Provisional application No. 63/358,416, filed on Jul. 5, 2022.

(51) Int. Cl.
| | |
|---|---|
| *A61B 8/02* | (2006.01) |
| *A61B 5/021* | (2006.01) |
| *A61B 5/11* | (2006.01) |
| *A61B 5/366* | (2021.01) |

(52) U.S. Cl.
CPC .............. *A61B 8/02* (2013.01); *A61B 5/021* (2013.01); *A61B 5/1107* (2013.01); *A61B 5/366* (2021.01); *A61B 2560/0228* (2013.01)

(58) Field of Classification Search
CPC ........... A61B 8/02; A61B 5/366; A61B 5/021; A61B 5/1107; A61B 2560/0228
See application file for complete search history.

(56) References Cited

U.S. PATENT DOCUMENTS

| | | |
|---|---|---|
| 7,054,679 B2 | 5/2006 | Hirsh |
| 7,267,649 B2 | 9/2007 | Zdeblick |
| 7,657,306 B2 | 2/2010 | Hirsh |
| 7,689,283 B1 | 3/2010 | Schecter |
| 7,761,141 B2 | 7/2010 | Hirsh |
| 8,843,194 B2 | 9/2014 | Hirsh |
| 2007/0191724 A1 | 8/2007 | Hirsh |
| 2007/0191901 A1* | 8/2007 | Schecter ............ A61N 1/36521 |
| | | 607/17 |
| 2010/0168578 A1 | 7/2010 | Garson et al. |
| 2010/0262206 A1 | 10/2010 | Zdeblick et al. |
| 2014/0121549 A1 | 5/2014 | Claus et al. |
| 2015/0359489 A1 | 12/2015 | Baudenbacher |
| 2018/0098709 A1 | 4/2018 | Hirsh |
| 2019/0183579 A1 | 6/2019 | Kosior et al. |
| 2019/0184172 A1* | 6/2019 | Ardell .................... A61N 1/362 |

OTHER PUBLICATIONS

Title: American Society of Anesthesiologists Abstract Published by: Robert A. Hirsh, M.D., Marc C. Torjman, Ph.D., Roy D. Goldfarb, Ph.D., Dated: Oct. 15, 2011.

(Continued)

*Primary Examiner* — Gerald Johnson

(74) *Attorney, Agent, or Firm* — Gregory J. Winsky, Esq.; ARCHER & GREINER, P.C.

(57) ABSTRACT

The system and method described provides for the non-invasive detection and quantification of systolic and diastolic heart failure, including subclinical, not-yet symptomatic systolic and diastolic heart failure.

14 Claims, 5 Drawing Sheets

(56) References Cited

OTHER PUBLICATIONS

Title: Biostamp Temporary Tattoo Electric Circuits by MC10 Published in: Dezeen Magazine URL: htp://www._dezeen.com/2013/03/28/biostamp-temporary-tattoo-wearable-electronic-circuits-john-rogers-mc10/ Dated: Mar. 28, 2013.

Title: Heart Activity Monitoring on Smartphone Published by: Anh Dinh Published in: 2011 International Conference on Biomedical Engineering and Technology, PCBEE vol. 11 (2011)© (2011) IACSIT Press, Singapore.

Title: Detection of S1 and S2 Heart Sounds by High Frequency Signatures Published by: D. Kumar, P. Carvalho, M. Antunes, J. Henriques, L. Eugenio, R. Schmidt, J. Habetha Published in: Proceedings of 28th IEEE EMBS Annual International Conference Published City: New York, USA Dated: Aug. 20-Sep. 3, 2006.

Title: Influence of Altered Inotrophy and Lusitrophy on Ventricular Pressure-Volume Loops Published by: Arnold M. Katz, MD, FACC Published In: Basic Concepts in Cardiology; JACC vol. 11, No. 2 Dated: Feb. 1988.

Title: The Long QT Syndrome: Importance of Phonocardiography and Ergometry Published by: E. Dupasquier and A. Nicole, L. Pinget Published in: U.S. National Library of Medicine National Institutes of Health URL: http:/www.ncbi.nlm.nih.gov/pubmed/2880395 Dated: Jan. 3, 1987.

Title: Structural Relationships Between Measures Based on Hear tBeat Intervals: Potential for Improved Risk Assessment Published by: Alfred P. Hallstome, Phyllis K. Stein, Raphael Schneider, Morrison Hodges, Georg Schmidt and Kurt Ulm Published in: IEEE Transactions on Biomedical Engineering, vol. 51, No. 8.

Title: Development of a Secure Body Area Network for a Wearable Physiological Monitoring System Using a PSoC Processor Published by: N. Sriraam, S. Swathy and S. Vvijayalakshmi Published in: Journal of Medical Engineering & Technology Dated: 2012; 36: 26-33.

Title: Relationships Between the Electrocardiogram and Phonocardiogram: Potential For Improved Heart Monitoring Published by: L.S. Stodieck and M.W. Luttges Published in: ISA Transactions, vol. 23, No. 4 Dated: 1984.

Title: Le Syndrome QT Long: Importance de la Phonocardiographie et de l'ergomatric Published by: E. Dupasquier, A. Nicole and L. Pinget Published in: Schweizerische Medizinische Wochenschrift Journal; 17-22 Dated: 1987 Published Location: France.

Title: A Survey on Wearable Sensor-Based Systems for Health Monitoring and Prognosis Published by: Alexandros Pantelopoulos and Nikalaos G. Bourbakis Published in: IEEE Transactions on Systems, Man and Cybernetics—Part C: Applications and Reviews, vol. 40, No. 1 Dated: Jan. 2010.

International Search Report, dated Aug. 16, 2023 for PCT/US2023/012384.

Eichhorn, et al—Are Contraction and Relaxation Coupled in Patients With and Without Congestive Heart Failure? Jun. 1, 1992 (Jun. 1, 1992). [retrieved on Jun. 27, 2023]. Retrieved from the Internet: <URL:https://www.ahajournals.org/doi/pdf/10.1161/01.CIR.85.6.2132> pp. 2132-2139.

* cited by examiner

NON-INVASIVE SYSTEM AND METHOD FOR DETECTING AND ACCURATELY QUANTIFYING SUBCLINICAL AND CLINICAL SYSTOLIC AND DIASTOLIC HEART FAILURE

CROSS REFERENCE TO RELATED APPLICATION

This application claims the benefit of U.S. Provisional Patent Application No. 63/358,416 filed on Jul. 5, 2022.

FIELD OF THE INVENTION

The aim of the instant invention is to provide for the non-invasive detection and quantification of systolic and diastolic heart failure, including subclinical, not-yet symptomatic systolic and diastolic heart failure. In this regard, the instant invention is a new way to process and derive clinical meaning and prognoses from physiomic data. The invention is predicated upon extracting data that is shown graphically in the well-known Wiggers Diagram (hereinafter the "Wiggers Diagram") which shows the entire cardiac cycle with simultaneous data streams, the ECG, phonocardiogram, and Left Ventricular Pressure. See https://commons.wikimedia.org/wiki/File:Wiggers_Diagrams.svg

BACKGROUND OF THE INVENTION

The present state of the art uses two-dimensional ultrasound imaging to measure parameters such as ejection fraction (which is not invariant with respect to Afterload or Preload) myocardial strain, and myocardial strain rate. These prior art measurements are entirely mechanical and utterly ignore the complex and interactive electrical and patho-electrophysiological character of the transduction dysfunction in systolic and diastolic heart failure. The patho-electrophysiological character of such dysfunction involves the rapid and massive movement of Calcium ions out of one cellular compartment, the sarcoplasmic reticulum, and into the cytosol, and then following a brief pause, very rapidly, movement right back into the sacroplasmic reticulum, with each heartbeat. Present methods ignore the ion trans-membrane flux features of the disease, and only quantify the mechanical features of the disease. Membrane Flux of Ions is to a great extent represented by the reciprocal of (E–M), that is 1/(E–M), in sec^−1. The quantity 1/(E–M), in both Systole and Diastole is essentially a membrane calcium ion flux transduction speed or rate in Systole, in 'transductions per second', and a 'de-transduction rate' in Diastole. And so present measures are effectively blind to half the physiologic features of Heart Failure, either Systolic or Diastolic, a significant defect.

As such, the present methods of diagnosis and quantification only serve to characterize and quantify symptoms in people who are already stricken with the illness, and who are living with symptoms. These methods are not sensitive or reliable enough to serve as a screening test for people who have subclinical or preclinical disease, screening for which is not now done. If a test for 'Pre-HF'—analagous to the use of HbA1c detect 'Pre-Diabetes'—were feasible, it may reveal opportunities to intervene earlier in the natural history of HF with drugs such as afterload reducers, with decreasing salt intake, and with fluid management in a way that may prolong life, improve the quality of life, and modify the natural history of the disease. The feasibility of such a test would also serve to save the healthcare system a great deal of money otherwise spent on frequent re-hospitalizations for acute decompensation of HF, requiring expensive ICU stays with endotracheal intubation and mechanical ventilation. Even in patients with known clinical HF, a metric that combines electrical with mechanical character over a full range of possible contractile states would be more accurate, and reproducible, and physiologically meaningful.

SUMMARY OF THE INVENTION

As stated above, an aim of the instant invention is the non-invasive detection and quantification of systolic and diastolic heart failure, including subclinical, not-yet symptomatic systolic and diastolic heart failure. The instant invention is a new way to process and derive clinical meaning and prognoses from physiomic data. The invention is predicated upon extracting data that is shown graphically in the Wiggers Diagram which shows the entire cardiac cycle with simultaneous data streams, the ECG, phonocardiogram, and Left Ventricular Pressure.

The Wiggers Diagram shows the relation between the Q-wave, which is where the second derivative of the ECG in systole is maximum, and the S1 heart sound, which is slightly delayed in time. This time interval is (E–M)ino, or the Intropic Electrical Mechanical Interval. Taking the point in the T-wave at which it first manifests maximal upward acceleration, and then noting the time delay to the S2 heart sound, identifies (E–M)lusi, or the Lusitropic Electrical-Mechanical Interval. When a Seismocardiogram, obtained with a precordial accelerometer, is available, then either the seismo signal that corresponds to S1 and S2, or its peak derivative values can serve as 'M' in the Systolic or Diastolic Electrical Mechanical Interval, (E–M) respectively. The ratio 1/(E–M) can be understood as a speed of electro-mechanical transduction, either inotropic or lusitropic. It has been shown that the speed of electromechanical transduction in cardiac systole (or de-transduction in cardiac diastole) is linearly proportional to the natural log of the magnitude of the strain rate, either systolic or diastolic, obtained from a 2D transthoracic echo machine, in systole, or diastole, respectively, as was described in the inventor's earlier patent applications that are identified herein.

Experimental results obtained by the inventor from dobutamine stress tests with a new metric of inotropic and lusitropic function, the Electrical Mechanical Intervals (E–M)ino and (E–M)lusi, have yielded two sets of linear individual calibration curves relating ln(strain rates) to 1/(E–M). Five evaluable subjects were studied. One set of five Calibration Curves describes systolic function for each of the five subjects, and the other set of five curves describe diastolic function, both for the same five individual subjects. The calibration curves are of the form ln(Strain Rate)=a+b/(E–M) where 'a' and 'b', the y-intercept and the slope, are constants for a given individual. (E–M)ino is used for the Systolic case, and (E–M)lusi is used for the Diastolic case. For both the Systolic and the Diastolic cases, plotting the y-intercept 'a' as a function of the slope 'b' for all five subjects results in a downward sloping line of intercept 'p' and slope 'q', with a very high correlation coefficient, called an "Intercept-Slope Tradeoff Function." There is one 'Intercept-Slope Tradeoff Function' for the systolic case, and another for the diastolic case, the only difference being the values of the intercept 'p' and the slope 'q'.

DETAILED DESCRIPTION OF THE INVENTION

Figure 1:
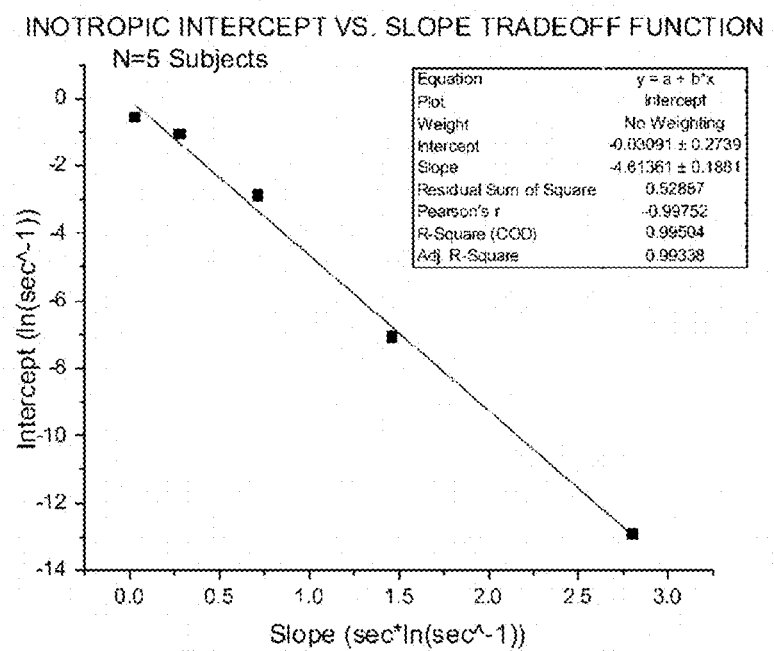
FIG. 1 is a cartesian coordinate mapping of the relationship between inotropic intercept and the slope tradeoff function for five healthy subjects as described herein.

As stated above, the aim of the instant invention is the non-invasive detection and quantification of systolic and diastolic heart failure, including subclinical, not-yet symptomatic systolic and diastolic heart failure. The instant invention is a new way to process and derive clinical meaning and prognoses from physiomic data. The invention is predicated upon extracting data that is shown graphically in the Wiggers Diagram which shows the entire cardiac cycle with simultaneous data streams, the ECG, phonocardiogram, and Left Ventricular Pressure.

The Wiggers Diagram shows the relation between the Q-wave, which is where the second derivative of the ECG in systole is maximum, and the S1heart sound, which is slightly delayed in time. This time interval is (E−M)ino, or the Intropic Electrical Mechanical Interval. Taking the point in the T-wave at which it first manifests maximal upward acceleration, and then noting the time delay to the S2 heart sound, identifies (E−M)lusi, or the Lusitropic Electrical-Mechanical Interval. When a Seismocardiogram, obtained with a precordial accelerometer, is available, then either the seismo signal that corresponds to S1 and S2, or its peak derivative values can serve as 'M' in the Systolic or Diastolic Electrical Mechanical Interval, (E−M) respectively. The ratio 1/(E−M) can be understood as a speed of electromechanical transduction, either inotropic or lusitropic. It has been shown that the speed of electromechanical transduction in cardiac systole (or de-transduction in cardiac diastole) is linearly proportional to the natural log of the magnitude of the strain rate, either systolic or diastolic, obtained from a 2D transthoracic echo machine, in systole, or diastole, respectively, as was described in the inventor's earlier patent applications that are identified herein.

Experimental results obtained by the inventor from dobutamine stress tests with a new metric of inotropic and lusitropic function, the Electrical Mechanical Intervals (E−M)ino and (E−M)lusi, have yielded two sets of linear individual calibration curves relating ln(strain rates) to 1/(E−M). Five evaluable subjects were studied. One set of five Calibration Curves describes systolic function for each of the five subjects, and the other set of five curves describe diastolic function, both for the same five individual subjects. The calibration curves are of the form ln(Strain Rate)=a+b/(E−M) where 'a' and 'b', the y-intercept and the slope, are constants for a given individual. (E−M)ino is used for the Systolic case, and (E−M)lusi is used for the Diastolic case. For both the Systolic and the Diastolic cases, plotting the y-intercept 'a' as a function of the slope 'b' for all five subjects results in a downward sloping line of intercept 'p' and slope 'q', with a very high correlation coefficient, called an "Intercept-Slope Tradeoff Function." There is one 'Intercept-Slope Tradeoff Function' for the systolic case, and another for the diastolic case, the only difference being the values of the intercept 'p' and the slope 'q'.

Figure 2:
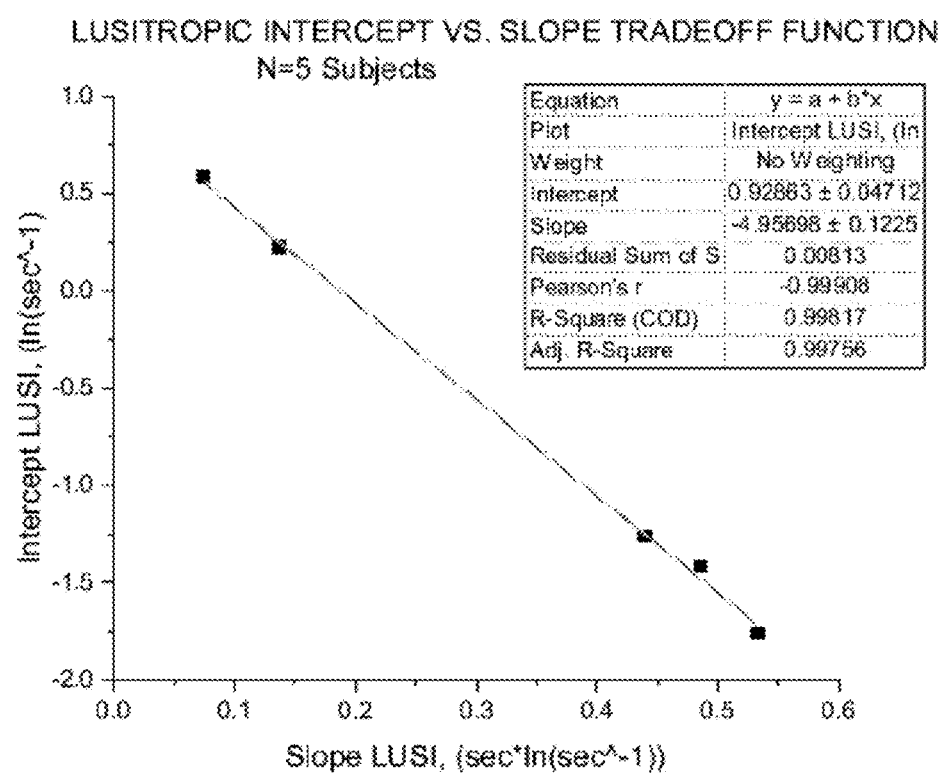
FIG. 2 is a cartesian coordinate mapping of the relationship between lusitropic intercept and the slope tradeoff function for five healthy subjects as described herein.

FIG. 1 shows the Intercept-Slope Tradeoff Function for the Inotropic case, and FIG. 2 shows the Intercept-Slope Tradeoff Function for the Lusitropic case, both of the form Intercept=p−q(Slope). It should be clearly understood that the resulting straight lines plotted in FIG. 1 and FIG. 2 represent the upper parametric boundaries of healthy normal Cardiac Systolic and Diastolic Function, respectively. This is true without regard to the weight, height, age, or gender of the subjects, over a wide range, since the Strain Rates describe the function of healthy myocardial tissue, irrespective of size or geometry, or the patient's height, weight, gender, or age. In this application each of these calibration curves are referred to as the "Universal Tradeoff Function for Inotropic Function" and the "Universal Tradeoff Function for Lusitropic Function," respectively. Specificity as to the creation of the Universal Tradeoff Function for Inotropic Function and the Universal Tradeoff Function for Lusitropic Function is set forth in through hereinbelow.

The Systolic and Diastolic Function upper boundaries obtain across the entire physiologic range of catacholamine receptor activation, and concomitant levels of Inotropy and Lusitropy. Such global metrics of Systolic and Diastolic Function, expressed over the entire physiologic range of Inotropy and Lusitropy are entirely novel and useful, compared to the present state-of the art, such as Ejection Fraction at rest. These metrics incorporate clinical information over the entire range of an individual patient's ability to compensate for whatever stresses that he encounters in daily life. The fitting parameters of the Tradeoff Functions (p,q) may well prove to be true for individual cardiomyocytes, or some random population of cadiomyocytes. The five subjects are of highly varied age, weight, height, and both genders are represented. The main thing the subjects have in common is that they all have healthy natural myocardial tissue. These linear 'Universal' or 'Population' parameters p, q—one each for the systolic and diastolic cases—are indicative of healthy myocardial tissue as it is put through its paces in a dobutamine stress test. The parameters are accurate representations relating to the performance of heart muscle globally, and also as to the small longitudinal muscle segments that are averaged in the proprietary algorithm by the 2D Echo device manufacturer to calculate the strain rates. It is anticipated that the fitting parameters of the Intercept-Slope Tradeoff Functions (p, q) also accurately describe individual cardiomyocytes, or any arbitrarily large random statistical sample of individual myocytes. If someone were to have heart failure (HF), whether systolic or diastolic, then for a given slope to the individual calibration curve, it follows that for all values of 1/(E−M), each point on the calibration curve will have a ln(Strain Rate) value below that of an individual whose myocardial tissue is healthy and normal. Another way of saying that, algebraically, is to say that, in HF, the y-intercept of the heart failure patient's individual calibration curve is lower than that for known normal hearts. In a two dimensional {Intercept, Slope} space, we can represent each individual calibration curve uniquely as a single point in said two-dimensional vector space in which the Intercept vs. Slope tradeoff function is represented. It follows that an accurate and reproducible degree of HF pathology is given by the vertical distance between the point (b,a) representing an afflicted individual's calibration curve, and a line representing all possible normal calibration curves. And that line is the Tradeoff Function. If an individual has no symptoms, and this vertical distance from the universal line to the individual point is still measurable and significantly exceeds the limits of measurement error, however small, we can use it to detect and quantify preclinical disease, and alter our clinical management accordingly. This approach has the potential to identify people with systolic and/or diastolic Heart Failure very early in the natural history of their disease, in analogy with the ability of a HbA1c assay of blood to predict who will go on to develop, or who is at risk to develop diabetes, a condition now understood as "pre-diabetes." Essentially, this technology represents a new, and very sensitive assay of Inotropic and Lustropic Function and therefore represents a way for the first time to detect and measure 'Pre-HF'.

The present state of the art uses two-dimensional ultrasound imaging to measure parameters such as ejection fraction (which is not invariant with respect to Afterload or Preload) myocardial strain, and myocardial strain rate. These prior art measurements are entirely mechanical and utterly ignore the complex and interactive electrical and patho-electrophysiological character of the transduction dysfunction in systolic and diastolic heart failure. The patho-electrophysiological character of such dysfunction involves the rapid and massive movement of Calcium ions out of one cellular compartment, the sarcoplasmic reticulum, and into the cytosol, and then following a brief pause, very rapidly, movement right back into the sacroplasmic reticulum, with each heartbeat. Present methods ignore the ion trans-membrane flux features of the disease, and only quantify the mechanical features of the disease. Membrane Flux of Ions is to a great extent represented by the reciprocal of (E–M), that is $1/(E-M)$, in $sec^{-1}$. The quantity $1/(E-M)$, in both Systole and Diastole is essentially a membrane calcium ion flux transduction speed or rate in Systole, in 'transductions per second', and a 'de-transduction rate' in Diastole. And so present measures are effectively blind to half the physiologic features of Heart Failure, either Systolic or Diastolic, a significant defect. As such, the present methods of diagnosis and quantification only serve to characterize and quantify symptoms in people who are already stricken with the illness, and who are living with symptoms. These methods are not sensitive or reliable enough to serve as a screening test for people who have subclinical or preclinical disease, screening for which is not now done. If a test for 'Pre-HF'- analagous to the use of HbA1c detect 'Pre-Diabetes'—were feasible, it may reveal opportunities to intervene earlier in the natural history of HF with drugs such as afterload reducers, with decreasing salt intake, and with fluid management in a way that may prolong life, improve the quality of life, and modify the natural history of the disease. The feasibility of such a test would also serve to save the healthcare system a great deal of money otherwise spent on frequent re-hospitalizations for acute decompensation of HF, requiring expensive ICU stays with endotracheal intubation and mechanical ventilation. Even in patients with known clinical HF, a metric that combines electrical with mechanical character over a full range of possible contractile states would be more accurate, and reproducible, and physiologically meaningful.

The method and system of the instant invention geometrically and simply defines the relation between the electrical and the mechanical character of transduction and tension development in normal healthy myocardial tissue. Present approaches only speak to the mechanical character of heart wall motion, contraction, or lengthening with loss of tension or filling. The prior art approach essentially ignores the pathophysiology of the disease which clearly has both electrical and mechanical features. The graphical simplicity of the instant invention makes it easy and obvious to tell when electrical and/or mechanical dysfunction resulting in HF is present, and as such provides a method making such an analysis easily and reproducibly quantifiable. The simplicity of the instant approach is analogous to the simplicity with which a pediatrician plots a child's height and weight on a growth chart. The growth chart is Universal, and stratified by percentiles. The patient's height or weight is plotted as a single point in time, or as multiple points over time. What is revealing is the deviation from the universal standards. The prior art approach to quantifying systolic or diastolic heart failure is entirely mechanical in character. This approach ignores important features of the disease and relations between features of the disease. The present invention enables clinicians to detect "Pre-HF" in a method analogous to the way in which "Pre-diabetes" is now diagnosed, providing opportunities for fluid, electrolyte, diet, and exercise as well as pharmacologic intervention before the subclinical goes to the clinical and the patient needs intubation and mechanical ventilation, ventricular assist devices, or a heart transplant.

This process of management can be effectively monitored and adjusted in real time, using the wearable electronic and mechanical technology to measure, transmit, and process (E–M)ino and (E–M)lusi described in U.S. Pat. No. 10,085, 665 (the "'665 patent") and U.S. Pat. No. 10,918,300 (the "'300 patent"), and the related divisional application described in the published US application US 2021/0128047 (the "'047 application"). The preventive approach described herein is much cheaper than the conventional approach that requires multiple hospitalizations for decompensation of congestive heart failure. This preventive approach based on the instant invention may utilize wearable technology, such as the electromechanical system shown in the '665 patent, the '300 patent, and the '047 application. Such an electromechanical system may operate under the control of the programs of the methods and algorithms described in the '665 patent, the '300 patent, and the '047 application, which methods in conjunction with such system puts early detection and prevention at low cost into the clinician's toolkit.

Heart failure is generally characterized as Systolic (HF without preserved Ejection Fraction) or Diastolic (HF with preserved Ejection Fraction). Assume a patient undergoes a dobutamine stress test at several increasing rates of dobutamine infusion at steady state. And further assume that ln(Strain Rate) in cardiac systole and diastole, along with the simultaneous values of $1/(E-M)$ino and $1/(E-M)$lusi are measured and graphed to create a linear calibration curve of ln(Systolic Strain Rate) vs $1/(E-M)$ino and another linear calibration curve of ln(Diastolic Strain Rate) vs. $1/(E-M)$ lusi, and that slope b and a y-intercept a are calculated for each. By plotting the Systolic Values of a and b as a point (b,a), with slope on the x-axis, and intercept on the y-axis on the graph in FIG. 1, and the Diastolic Values of a and b as a point (b,a) on the graph in FIG. 2, it may well be the case that both points are below their respective Universal or Intercept-Slope Tradeoff Function lines in both graphs. Measuring the vertical distance between these points and their respective lines, parallel to the y-axis—whose units are $ln(sec^{-1})$, that is, units of ln(Strain Rate)—yields a precise and reproducible metric of Systolic Heart Failure from FIG. 1, and Diastolic Heart Failure in FIG. 2. In other words, it may turn out that the patient has both Diastolic Heart Failure AND Systolic Heart Failure, and in different degrees, which change measurably with respect to one-another over time during the five-year course of the natural history of this disease. Improvements in performance with therapy can be accurately tracked in this way as well. This alone is an enormous advantage over the metrical and monitoring status quo.

Let the vertical distance between the Universal Inotropic Intercept-Slope Tradeoff Function (FIG. 1) and the single point denoting the Intercept and Slope of an individual patient's ln(Systolic Strain Rate) vs.1/(E−M)ino Calibration Curve be referred to herein as VDino. And let the vertical distance between the Universal Lusitropic Intercept-Slope Tradeoff Function and the single point denoting the Intercept and Slope of the same patient's Lusitropic ln(Diastolic Strain Rate) vs.1/(E−M)lusi Calibration Curve be referred to herein as VDlusi. Note that the units of both VDino and VDlusi are ln(Sec^−1), or ln(Strain Rate).

So, we can write F=VDino/VDlusi where F is the Ratio of the log of Systolic Dysfunction to the log of Diastolic Dysfunction, and T=VDino+VDlusi where T is the Total Systolic and Diastolic Dysfunction in a patient suffering from Heart Failure. It should be noted that in the alternative, it is possible to plot (VDino, VDlusi) on (x, y) axes, and add them vectorially while noting the angle between the x axis and the vector.

This angle Theta is given by the equation; tan(Theta)= VDlusi/VDino

The magnitude of the vector is given by the equation: VDtotal=(VDino^2+VDlusi^2)^1/2

The angle Theta makes a quantitative graphical statement about the contributions of Diastolic (Y-axis) and Systolic (X-axis) dysfunction to the clinical picture of HF, and about which form of myocardial dysfunction, Systolic or Diastolic predominates in the clinical picture. If Theta<45 degree then Systolic Dysfunction prevails. If Theta>45 degrees, then Diastolic Dysfunction prevails. The magnitude of the vector is a measure of the extent of the total size of the Heart Failure problem being diagnosed and treated. Over time, changes in the vector would reveal objective changes in the severity and character of the condition, just like the analogous pediatrician's growth chart referenced hereinabove.

This approach allows the health care professional to make an assessment of the risk of Heart Failure on a firmer quantitative and more accurate and reproducible footing than what obtains in the present state of the art.

One should note a second observation regarding FIGS. 1 and 2: plotting each of the straight lines together on the same graph, the Lusitropic Intercept-Slope Tradeoff Function would be a downward sloping line drawn above the Inotropic Intercept-Slope Tradeoff Function by 0.92863−(−0.03091)=0.96773 ln(sec^−1), This is on the order of 1 log unit. The slopes in FIGS. 1 and 2, that is, −4.613614.95698, are roughly equal within the limits of experimental error.

This graphical representation can be seen to evidence that Strain Rates in healthy patients are significantly faster in Cardiac Diastole than in Systole. A normal heart relaxes faster than it squeezes. This human data is consistent with data published in 2011 by the inventor of this instant invention determined by using a pressure catheter in the left ventricle of septic pigs and comparing the absolute magnitude of the maximum value of the first derivative of Left Ventricular Pressure, LVP'(t) max, in Cardiac Systole with that of Diastole over many hours, before and after the placement of a septic clot of *E. coli* in the peritoneum of the pig. See the inventor's 2011 abstract titled "Lusitropic/Inotropic Relation in Porcine Septic Shock: An Early Biomarker of Cardiodynamic Decompensation?" published by the American Society of Anesthesiologists.

In healthy animals LVP'(t)max is larger in magnitude in Cardiac Diastole than in Systole, though its direction of motion is opposite. Then as the sepsis progresses, that circumstance inverts, and their ratio of LVP' Distole/LVP' Systole which started out greater than 1, subsequently crashes through the value of 1 even as the pig's heart becomes hyperdynamic, struggling to compensate for the loss of SVR and Blood Pressure as Sepsis evolves. Further unpublished reduction of the same pig data referenced in the above showed a linear relation between ln(LVP'(t)max) and 1/(E−M) in both the Inotropic and the Lusitropic cases. Since both ln(LVP'max) and ln(Strain Rate) are linearly proportional to 1/(E−M), it follows that both ln(LVP'max) and ln(Strain Rate) are linearly proportional to each other. So ln(LVP'max), the maximum rate of change in the pressure inside the Left Ventricle and ln(Strain Rate) can be understood to be alternative metrics of Inotropy and Lusitropy. Only the size of the fitting parameters, Slope and Intercept change if we were to use ln(LVP'(t)max) in preference to ln(Strain Rate). Of course, Strain Rate has the enormous advantage of being non-invasively measured.

As to the complement of drawings set forth in this application, a further detailed description follows for each:

FIG. 1 shows a summary of the Inotropic Calibration Curves of 5 healthy subjects of diverse heights, weights, and ages, undergoing a Dobutamine Stress test while simultaneously measuring 1/(E−M)ino and ln(abs(Systolic Strain Rate)). This figure shows the Universal Tradeoff Function for Inotropic Function. Each of the 5 points shown represents an individual subject. Each point is of (b,a) where b is the slope and a is the y-intercept of the individual subject's Linear Inotropic Calibration Curve. The curve has the form ln(abs(Systolic Strain Rate))=a+b/(E−M)ino. This downward sloping function shown in the figure is called the Inotropic Intercept-Slope Tradeoff Function. It is anticipated that this Tradeoff Function will obtain for an arbitrarily large sample of individuals in good cardiovascular health and fitness. Moreover, the fitting parameters (p,q)=(Intercept, Slope) of this Inotropic Intercept-Slope Tradeoff Function are considered to be reasonable approximations to Universal Parameters of Inotropic Function in healthy myocardial tissue.

It is anticipated that a patient with heart failure will have a Linear Inotropic Calibration Curve at some point (b,a) below the line shown in the Tradeoff function above. The Vertical Distance between this point and the Tradeoff function is VDino, which is a metric of Systolic Dysfunction in Heart Failure. Moreover, the fitting parameters (p,q)=(Intercept, Slope) of this Inotropic Intercept-Slope Tradeoff Function are considered to be reasonable approximations to Universal Parameters of Inotropic Function in healthy myocardial tissue.

FIG. 2 shows a summary of the Lusitropic Calibration Curves of the same 5 healthy subjects shown in FIG. 1. This figure shows the Universal Tradeoff Function for Lusitropic Function. These 5 healthy subjects are of diverse heights, weights, and ages, undergoing a Dobutamine Stress test while simultaneously measuring 1/(E−M)lusi and ln(Diastolic Strain Rate). Each of the 5 points shown represents an individual subject. Each point is of (b,a) where b is the slope and a is the y-intercept of the individual subject's linear Lusitropic Calibration Curve. The curve has the form ln(Diastolic Strain Rate)=a+b/(E−M)lusi. This downward sloping function shown in the figure is called the Lusitropic Intercept-Slope Tradeoff Function. It is anticipated that this Tradeoff Function will obtain for an arbitrarily large sample of individuals in good cardiovascular health and fitness.

Moreover, the fitting parameters (p,q)=(Intercept, Slope) of this Inotropic Intercept-Slope Tradeoff Function are considered to be reasonable approximations to Universal Parameters of Lusitropic Function in healthy myocardial tissue.

It is also anticipated that a patient with heart failure will have a Linear Lusitropic Calibration Curve at some point (b,a) below the line shown in the Tradeoff function shown above. The Vertical Distance between this point and the Tradeoff function is VDlusi, which is a metric of Diastolic Dysfunction in Heart Failure.

The instant invention implements a solution geometrically and, using easily understood linear functions, very simply defines the relation between the electrical and the mechanical character of transduction and tension development in normal healthy myocardial tissue. It can represent the systolic or diastolic character of someone's disease by the angle a vector or 'arrow' makes with the x-axis, and of the seriousness of the disease, compared to all healthy people, by the length of the arrow. Alternatively, it can represent the magnitude of the deficit in Inotropic or Lusitropic function as a quantitity that depends only on the vertical distance between a point that defines a given individual's Calibration Funtion in {Slope,Intercept} space, and a downward sloping linear function in that same space that defines normal cardiac health. Intropic health and Lusitropic health have similar, but separate normal population linear functions, which differ only in their fitting paramaters, that is, their slope, and intercept, which are universal parameters, and graphically very simple and easy to understand. Present approaches only speak to the mechanical character of heart wall motion, contraction, or lengthening with loss of tension or filling.

This present state-of-the-art essentially ignores the pathophysiology of a life-threatening and costly-to-care-for disease which clearly has both electrical and mechanical features. This graphical simplicity makes it easy and obvious to tell when electrical and/or mechanical dysfunction resulting in HF is present, and makes it easily and reproducibly quantifiable. The simplicity is analogous to the simplicity with which a pediatrician plots a child's height and weight on a growth chart. The growth chart is Universal, and stratified by percentiles. The patient's height or weight is plotted as a single point in time, or as multiple points over time. What is revealing is the the deviation from the Universal standards, given here by the Slope-Intercept Tradeoff Function.

The present approach to quantifying systolic or diastolic heart failure is entirely mechanical in character. This ignores important features of the disease and relations between features of the disease. The present invention will enable clinicians to detect 'Pre-HF' analagous to the way in which 'Pre-diabetes' is now diagnosed, providing opportunities for fluid, electrolyte, diet, and exercise as well as pharmacologic intervention before the merely subclinical state comes to clinical symptoms, and the patient needs intubation and mechanical ventilation, ventricular assist devices, or a heart transplant. This process of management can be effectively monitored and adjusted in real time, using the wearable technology to measure, transmit, and process (E−M)ino and (E−M)lusi described in previous disclosures.

This preventive approach is much cheaper than the present conventional multiple hospitalizations for decompensation of Congestive heart failure, and puts early detection and prevention squarely into the clinicians's diagnostic and management toolkit.

Heart Failure is generally characterized as Systolic (HF with reduced Ejection Fraction, HFrEF) or Diasatolic (HF with preserved Ejection Fraction, HFpEF). Assume a patient undergoes a dobutamine stress test at several increasing rates of dobtamine infusion at steady state. And further assume that ln(Strain Rate) in cardiac systole and diastole, along with the simultaneous values of 1/(E−M)ino and 1/(E−M)lusi are measured and graphed to create a calibration curve of ln(Systolic Strain Rate) versus the ratio 1/(E−M)ino and another calibration curve of ln(Diastolic Strain Rate) versus the ratio 1/(E−M)lusi, and that a slope B and a y-intercept A are calculated for each. If you plot the Systolic Values of (B,A) as a point on the graph in FIG. 3, and the Diastolic Values of (B,A) as a point on the graph in FIG. 4, it may well be the case that there is a distance between point (B,A) and the Tradeoff Function line in one or both the Systolic and Diastolic graphs. Measuring the vertical distance between these individual patient points and their respective lines, parallel to the y-axis—whose units are ln(sec^-1), that is, units of ln(Strain Rate)—will give us a precise and reproducible metric of Systolic Heart Failure from FIG. 3, and of Diastolic Heart Failure in FIG. 4. This is shown explicitly in FIG. 3 for the Systolic Case, and in FIG. 4 for the Diastolic Case. Set forth in [0016] through [0130] hereinbelow is additional specificity as to the creation of a patient's individual Tradeoff Function for Inotropic Function and the creation of a patient's individual Tradeoff Function for Lusitopic Function.

Figure 3:
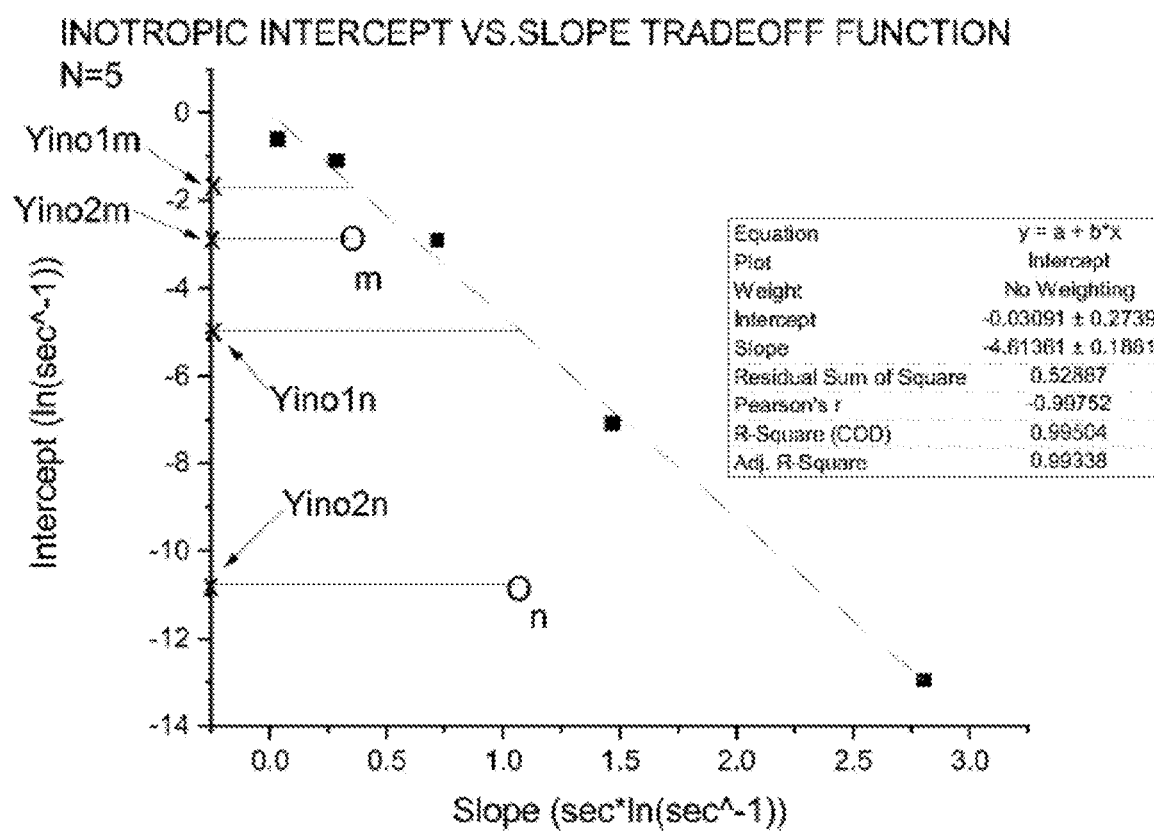
FIG. 3 plots the slope and intercept for individual patient "m" and individual patient "n" against the cartesian coordinate mapping of the relationship between inotropic intercept and the slope tradeoff function of FIG. 3.
Figure 4:
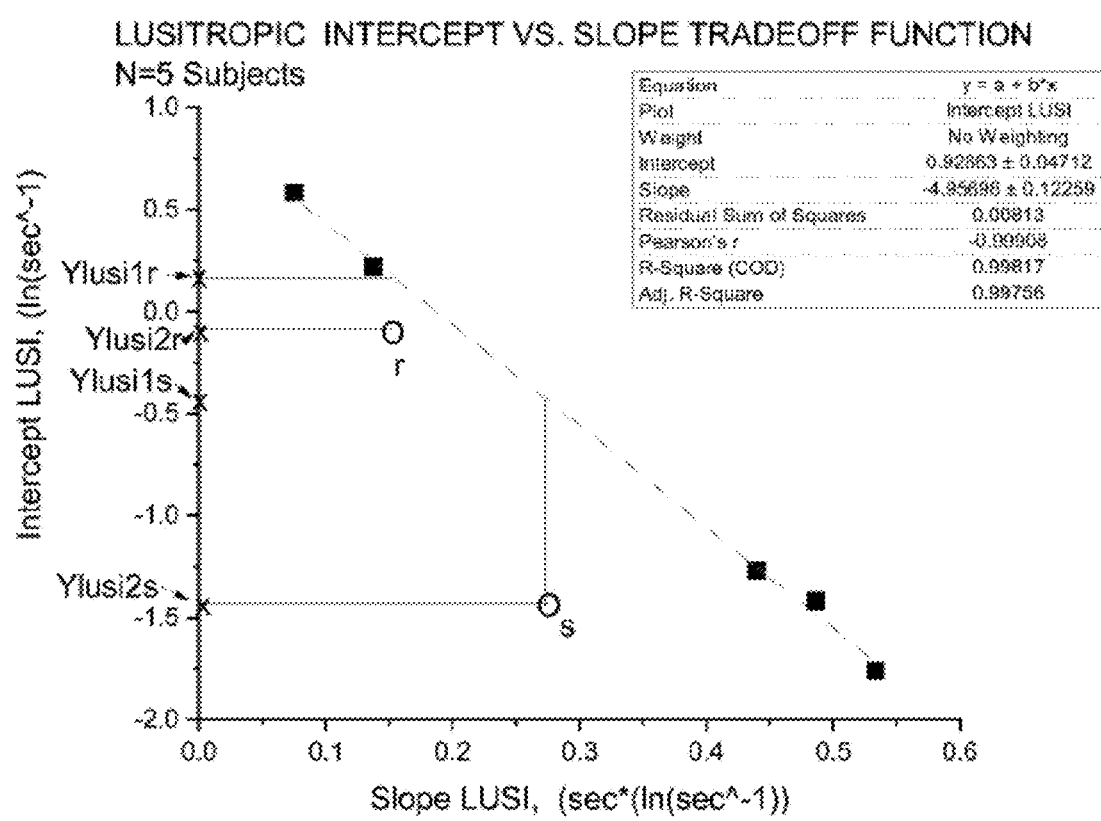
FIG. 4 plots the slope and intercept for individual patent "r" and individual patient "s" against the cartesian coordinate mapping of the relationship between lusitropic intercept and the slope tradeoff function of FIG. 4.

In other words, it may turn out that the patient has both Diastolic Heart Failure and Systolic Heart Failure, and in different degrees, which change measurably with respect to one-another over time during the five year course of the natural history of this disease. This presents an advantage over the metrical and monitoring status quo. FIGS. 3 and 4 show the same Universal Intercept vs. Slope Tradeoff Functions for the Systolic and Diastolic cases as were shown in FIGS. 1 and 2. Only now, in addition to the Universal Tradeoff Function, both FIGS. 3 and 4 also show two different individual patients, with very different levels of myocardial pathology, representing each patient as points in and n in the Inotropic case, and as points r and s in the Lusitropic case.

To review, each individual's point represents a slope and an intercept of a linear Calibration Curve that simply maps ln(Strain Rate) to 1/(E−M). Note that in both FIGS. 3 and 4, points in, and r are pretty close to the universal Tradeoff Function. While these patients may have no symptoms, the technology reveals that they have a deficit, however small, which separates them from the norm.

In both FIGS. 3 and 4, patients represented by points n (FIG. 3) and s (FIG. 4) are both suffering from the symptoms of Congestive Heart Failure. Patient n is suffering from Intropic Heart Failure, or HFrEF (Heart Failure with reduced Ejection Fraction) and Patient s is suffering from Lusitropic Heart Failuroe, or HFpEF (Heart Failure with preserved Ejection Fraction).

By using these graphs, and representing the individual patient as a point and comparing the position of that point to a norm defined by a line, we can learn a great deal about an individual's myocardial health, or lack thereof. In this way, it is possible to identify people who have subclinical disease, either inotropic or lusitropic, that is 'Pre-CHF' in a way that is not now being done. More importantly, we can categorize the deficit as inotropic or lusitroic, and we can accurately, reliably, and reproducibly quantify the deficit. That represents a significant improvement in the State of the Art.

Referring to FIG. 3 we can describe how to quantify the Inotropy of Patient in, shown at the point Yino2m. And we can plainly see what normal healthy Inotropy would looks like, at point Yino1m, for a given slope of the Calibration Curve. Yino1m is just a point on the line that defines the Inotropic Intercept-Slope Tradeoff Function. Note that both of these quantities, Yino1m and Yino2m, are natural logarithms of what the systolic strain rate would be in the abstract as the (E−M)ino interval gets extremely long, in the limit as it approaches infinity. That cannot happen physiologically, but the thought experiment in which it does happen is a useful metric of how much Inotropic Function patient in really has, given the slope of patient m's Calibration Curve.

The well known property of logarithms states that ln(b)−ln(a)=ln(b/a). So it follows that Yino2m−Yino1m=ln(Strain Rate 2m/Strain Rate1m). But the right hand side of that equation is just the natural log of the ratio of patient m's Calibration Curve Y-intercept A, over the Calibration Curve Y-intercept A of a patient taken from the population of people whose myocardiums are perfectly healthy. So, we can think of the difference between Yino2m and Yino1m as a kind of Inotropic Fraction IF, that equals 1 when the patient we are comparing to the population of healthy people is himself perfectly healthy, and less than 1 if there is some deficit in Inotropic function. IF can be easily intuited by clinicians, just as the Ejection Fraction, EF, has been traditionally understood. Traditionally EF has been expressed as a percentage. But that is form, not substance.

So we can write, IF=exp(VDino)=exp(Yino2m−Yino1m). Note that VDino is a signed quantity, and here it is less than 0. From FIG. 3, we can clearly see that IF is slightly less than 1 for patient in, simply because the Vertical Distance, VDino=(Yino2m−Yino1m) is only slightly less than 0, and exp(0)=1

Now consider patient n in FIG. 3. Patient n has a Calibration Curve with a steeper slope than that of patient in, That means that a given change in 1/(E−M)ino creates a larger change in the ln(Systolic Strain Rate) for patient n than it did for patient in. By inspection, the difference between the population intercept for healthy people Yino1n, and the actual Y-intercept for patient n's Calibration Curve, Yino2n is Much bigger than it was for Patient in. Patient n is in trouble. He cannot lie flat in his bed without feeling short of breath. With a stethoscope you can hear rales at the base of both lungs. The patient is in Congestive Heart Failure, and needs diuretic therapy.

Again, the slope and intercept of patient m's calibration curve, shown as a point in FIG. 3 also summarizes and contains all the variables, such as age, sex, height, weight that you would ordinarily think go into determining the value of a quantity such as the Inotropic Fraction, IF.

Switching to FIG. 4, we can clearly see how the measurement of Lusitropy proceeds by analogy from the measurement of Inotropy. In FIG. 4 we see the Lusitropic Intercept vs. Slope Tradeoff Function for all possible Calibration Curves that are measured on a population of subjects who are known to enjoy excellent myocardial health. We see two individuals r and s, the slopes and intercepts of whose Calibration Curves are plotted in Lusitropic {Slope, Intercept} space as shown. Patient r has an Intercept, at a given Slope, that falls away from the Lusitropic Intercept vs. Slope Tradeoff Function that empirically defines myocardial health. The Vertical Difference, (or Vertical Distance) VDlusi=(Ylusi2r−Ylusi1r), and is a small number less than Zero. Patient r has no symptoms of CHF whatever. But, patient r bears watching by his medical provider, given that he has 'Pre-HFpEF' and bears monitoring. And that is simply because with hands-on management, lifestyle changes, exercise, fluid management, afterload reducers, it is possible to bend his morbidity curve in a way that will add years to his life and life to his years. All he and his clinicians need do is absorb the information from the monitoring system over time, over years, and as in the management of diabetes, 'close the loop'. This could serve the patient well, while saving the health care a great deal of money from reduced hospitalizations whose frequency increases over time like the frequency of the skips of a skipping stone, before it sinks.

So we can write that the Lusitropic Fraction, LF=exp(VDlusi)=exp(Ylusi2r−Ylusi1r). Note here that, graphically, VDlusi is a signed quantity whose magnitude is small, and less than 0. So it follows that exp(VDlusi) will be close to, but less than 1. And that makes sense, physiologically, since patient r has no symptoms, and his condition is pre-clinical.

Now consider patient s, shown below patient r in FIG. 4. Patient s is very sick. He can barely breath, and his problems are worse if he tries to walk. His lungs are congested, and he has trouble oxygenating himself on room air. But he is sick by a very different mechanism, with a pathophsiologically different pathway, than was patient n in FIG. 3. He is suffering from HFpEF, a failure of his myocardium to lose tension and relax when it is supposed to. This is an ATP requiring process, that is used to actively transport Ca++ ions from the cytosol, against the concentration gradient, away from the tropinin receptors, and back into the sarcoplasmic reticulum compartment, in anticipation of the next systole. That process requires Oxygen. Patient s's medical management, may, going forward, be different from that of patient n, as new approaches to the problem emerge over time.

But the point is, by using these measurements, (E−M)ino and (E−M)lusi in patients who are not necessarily hospitalized, who are ambulatory and living at large in their community, and using these simple graphical and algebraic conventions, we can tell the difference, we can quantify the difference, and we can track the difference. And by 'closing the loop' we can achieve better outcomes at lower costs, while simultaneously making the care easily accessible to anyone with a cellphone.

To complete the analogy, we can write that the Lusitropic Fraction, LF=exp(VDlusi)=exp(Ylusi2s−Ylusi1s). In this case of patient s, the Vertical Difference (or Difference) VDlusi is a significant quantity, on the order of (−1.5−(−0.5))=(−1.5+0.5)=−1 natural log units. So for patient s, LF=exp(−1)=1/2.718=0.368, which intuitively 'feels' like a low Ejection Fraction, except that it describes a clinical case of low Lusitropy, not Inotropy. Note: 'VD' in VDino and VDlusi stands for 'Vertical Distance', or better 'Vertical Displacement' since it matters that one starts with the smaller Y-intercept from the subject and then subtracts the larger Y-intercept from the population to get a number that is less than zero in case the subject has some disease, and zero if he has no disease whatever. IF and LF, the Inotropic Fraction and the Lusitropic Fractions, are the ratios of the individual's Observed Strain Rate from the Y-intercept to the Strain Rate from the Healthy Population's Y-intercept, at the given Slope of the individual's Calibration Curve. In this way, these fractions are a measure of Ejection Fraction, but for all possible values of 1/(E−M).

In summary, when we say that the Lusitropic Fraction LF=exp(VDlusi), or the Inotropic Fraction IF=exp(VDino) what we are saying is just this; Both IF and LF are the fraction of the Expected Strain Rate at the Y-intercept from a healthy population that is represented by the Observed Strain Rate at the Y-intercept derived from the Calibration Curve of an individual whose cardiac function is being assessed individually. VDino and VDlusi are signed quantities less than or equal to 0, which are clearly depicted and whose measurement is shown in FIGS. 3 and 4.

We can anticipate that some patients will have a 'mixed' picture of Intropic and Lusitropic Dysfunction. We can quantify the Total Myocardial Function Fraction, TMFF, by combining IF and LF in some physiologically meaningful way. Since Inotropy and Lusitropy are different, mutually inverse yet physiologically and pathophysiologically coupled processes, it may be helpful to think of LF and IF as mutually perpendicular vectors that operate on the same organ. So we can add IF and LF vectorially such that TMFF=[(IF)^2+(LF)^2]^1/2

The only drawback to this approach is that in a state of perfect Inotropic Health, IF=1, LF=1, and TMFF=2^(1/2), roughly 1.414. So it makes intuitive sense to normalize the magnitude of this vector by dividing by the square root of 2, so that a patient who enjoys perfect intropic and lusitropic health will have a TMFF=1.

So, we can write TMFF={[(IF)^2+(LF)^2]^1/2}/(2^(1/2)). The magnitude of the vector shows how big a Heart Failure problem you are dealing with. Over time, it would reveal objective changes in the severity and character of the condition, like the pediatrician's Growth Chart. The component metrics IF and LF could be tracked over time separately One could alternatively plot (IF, LF) on (x,y) axes, and add them vectorially while noting the angle between the x axis and the vector. The angle makes a quantitative graphical statement about the contributions of Diastolic (Y-axis) and Systolic (X-axis) function to the clinical picture of HF, and about which form of myocardial dysfunction, Systolic or Diastolic predominates in the clinical picture, serving to put the assessment of Heart Failure on a firmer quantitative and more accurate and reproducible footing than what obtains in the present state of the art.

Another observation about FIGS. 1 and 2; if one were to plot them on the same graph, the Lusitropic Intercept-Slope Tradeoff Function would be a downward sloping line drawn above the Inotropic Intercept-Slope Tradeoff Function by 0.92863−(−0.03091)=0.96773 ln(sec^−1), This is on the order of 1 log unit. That is very significant.

The slopes in FIGS. 1 and 2, that is, −4.61361 and −4.95698, are roughly equal within the limits of experimental error. Note that in the Inotropic Case the (E−M)ino intervals end at an 'M' event which is a first derivative peak. Not so in the Lusitropic Case where the 'M' event is the undifferentiated Seismocardiogram. That is arbitrary, and heuristic. Had the same convention been used in the Inotropic case, the 'M' event would occur a few milliseconds later, and the (E−M)ino interval would be longer, and 1/(E−M)ino would be smaller than had we used the undifferentiated Seismocardiogram signal. That would transform the x-axis in FIG. 1 to a smaller dimension, increasing the magnitude of the rise (in this case, the 'Fall' since the direction is negative) over the run, which would increase the magnitude of the negative slope. That, in turn, would bring the slope of FIG. 1 closer in line with the slope of FIG. 2.

That the intercepts in FIGS. 1 and 2 are significantly different suggests that Strain Rates in Health are always significantly faster in Cardiac Diastole than in Systole. A normal heart relaxes faster than it squeezes. This is consistent with unpublished data obtained in 2011 using a pressure catheter in the left ventricle of septic pigs and comparing the first derivative of LVP in Cardiac Systole with that of Diastole over many hours, before and after the placement of a septic clot of *E. Coli* in the peritoneum of the pig. In health, LVP'max is larger in magnitude in Cardiac Diastole than in Systole, though its direction of motion is opposite. Then as the sepsis progresses, that circumstance inverts, that is, the ratio of LVP'max Distole/LVP'max Systole starts out greater than 1 and later crashes through 1 even as the pig's heart becomes hyperdynamic while struggling to compensate for the loss of SVR and Blood Pressure as Sepsis evolves. (See ASA Abstracts Hirsh, Torjman, Goldfarb, 2011. See http://www.asaabstracts.com/strands/asaabstracts/ab stract.htm?year=2011 &index=4&absnum=5333.

It is also clear that LVP'max, which is the maximum value of the first derivative of Left Ventricular Pressure and Strain Rate in both Systole and Diastole are related a priori, since their natural logarithms are both linearly proportional to 1/(E−M) (unpublished data). Two quantities that are both linearly proportional to 1/(E−M) must be linearly proportional to one another. Only the fitting parameters, Slope and Intercept, will change, since ln(LVP'(t)max) and ln(Strain Rate) have different units.

Moreover, and to make this process explicitly clear, Since the recognition by the Cardiology community that loss of Lusitropic Function can cause Congestive Heart Failure, there has been a need to rename or 'rebrand' the more classical form of Congestive Heart Failure (CHF) due to loss of Systolic or Inotropic Function.

Historically, Congestive Heart Failure due to loss of Systolic Function-'Pump Failure'—was called 'Dropsy'. It was treated with drugs like digitalis, extracted from leaves of the Foxglove plant. This served to increase the tension in the left ventricle when it contracts. In the present, CHF is now more often treated with Afterload Reducers, like calcium channel blockers, that lower blood pressure and serve to reduce the work of the heart. That way, fluid doesn't back up into the lungs, which don't become congested. And the patient feels no shortness of breath, especially when lying flat on his back in bed.

At this time, Heart Failure due to loss of Systolic Function is called Heart Failure with reduced Ejection Fraction (HFrEF). That Ejection Fraction is reduced (causing a patient congestive symptoms, shortness of breadth, loss of oxygen saturation due to an increase in the diffusion barrier to oxygen transport across the swollen capillaries of the alveoli of the lungs, and fluid filling the alveoli so that the patient feels as though they are drowning) is clearly evident to any clinician equipped with a 2D Echocardiograph. The 2D Echocardiograph yields an image in full end-diastole, and also an image at end-systole. The echocardiographer then describes the ratio of the cross-sectional area of the left ventricle chamber in those two images using the fraction, End Systole/End Diastole. Hence the 'Ejection Fraction, (EF)'. In Systolic Heart Failure, the EF is reduced.

In Diastolic Heart Failure, the Left Ventricle is 'remodeled'. It can become thicker. It loses its compliance (dV/dP). It becomes stiffer as it fills with blood. It doesn't relax its tension or pressure (dP/dt) from end-systole nearly as fast as a heart in good health. In this circumstance, the patient is said to be in Heart Failure with preserved Ejection Fraction, HFpEF. Again, Ejection Fraction is an easy, intuitive measurement to make, and its preservation, or reduction serves to distinguish between the two kinds of Heart Failure, Systolic (Inotropic) and Diastolic (Lusitropic). Before 2D Echo devices became nearly as ubiquitous as laptop computers, clinicians didn't trouble themselves about this distinction.

Ejection Fraction is an imperfect proxy metric of Contractility. For instance, in High Afterload states, like when you give phenylephrine, the EF will be low, even if Contractility is normal. Conversely, in Low Afterload states, like Shock, EF will be high or even normal, even if there is a deficit in Contractility due to circulating bacterial toxins. A normal ejection fraction is 55% or higher.

The disclosure of the present application serves to provide for a method that very accurately and reproducibly quantifies whether Heart Failure is Lusitropic, or Inotropic, or both, and precisely how much the condition is due to Inotropic Failure, and precisely how much of the condition is due to Lusitropic Failure. The following procedure is used to make this very precise, taxonomic, diagnostic determination: (1) Perform a Dobutamine Stress Test on the patient with suspected Heart Failure or Sub-clinical Heart Failure, which has not yet gotten sufficiently bad so as to cause symptoms, but will do so over time if left untreated. In patients who are able, exercise can be used instead of Dobutmine. Using the procedure to detect Sub-clinical Heart Failure serves as a screening tool. This is not now possible in the present state-of-the-art. (2) Make simultaneous measurements of Strain Rates in Cardiac Systole and Cardiac Diastole with the 2D Echo, and corresponding measurements of (E–M)ino and (E–M)lusi, for several consecutive heartbeats, at rest, and repeat this at (at least) two increasing levels of Dobutamine infusion rate. Alternatively, the patient can be asked to exercise as they are able, in a metered fashion, such as the Bruce Protocol, on an inclined treadmill, at varying speed. The simultaneous measurements of Strain Rates and (E–M) can be made after a maximally exercising patient stops and quickly lies down. This will generate a Systolic Function Calibration Curve, with ln(abs(Systolic Strain Rate)) on the Y-axis, and 1/(E–M)ino on the X-axis. This is a monotonically increasing straight line, of Y-Intercept A1, and Slope B1. (3) It will also generate a Diastolic Function Calibration Curve, with ln(Diastolic Strain Rate) on the Y-axis, and 1/(E–M)lusi on the X-axis. This is a monotonically increasing straight line of Y-intercept A2 and slope B2. (4) Now plot (B1,A1) on the Universal Inotropic Intercept-Slope Tradeoff Function curve, described in the previous part of this Invention Disclosure. It will likely be below the downward sloping line that relates Intercept to Slope for all healthy myocardial tissue. Measure the vertical distance VDino between (B1,A1) [(Slope, Intercept)] and the Inotropic Intercept-Slope Tradeoff Function. This signed quantity VDino, < or =0, in units of ln(sec^−1), is an absolute numerical metric of the decrease in Inotropic function from Normal Health, if any, in this particular patient. VDino represents the natural logarithm of the ratio of the patient's Inotropic Function to that of healthy normal people whose Calibration Function has a slope equal to that of the individual patient's. The signed quantity VDino is calculated by subtracting the normal healthy Intercept given by the Tradeoff Function for a given slope from the individual patient's Calibration Curve Intercept, A1. By the property of logarithms where ln(a/b)=ln(a)−ln(b), the signed difference VDino raised as an exponent of the transcendental number e (roughly 2.178 . . . ) yields the ratio of the patient's Inotropic Function to that of a normal healthy heart whose slope equals that of the individual patient's. Since VDino is negative, or 0, and the Inotropic Fraction IF=exp(VDino), it follows that IF has to be <1 or =1. VDino might be empirically real and measurable, but as yet, sub-clinical. If so, detecting and quantifying that represents an opportunity to intervene on a preventive basis, so as to conserve Inotropic Function over time. (5) Analogously, perform the same operation in the Lusitropic case. Plot the (Slope, Intercept) point (B2, A2) from the Calibration Curve, on the Universal Lusitropic Intercept-Slope Tradeoff Function. It will be, analogously, below the line. Measure the Vertical Distance, VDlusi (which is signed and < or =0 as described in the above) from the Universal Lusitropic Intercept-Slope Tradeoff Function Curve, to the point (B2, A2), for a slope given by that of the individual patient's Lusitropic Calibration Curve.

This signed quantity, VDlusi, also measured in units of ln(sec^−1), is a precise, reproducible metric of the decrease in Lusitropic Function, if any, suffered by this particular patient. It too, may be empirically real, but, as yet, sub-clinical. We define the Lusitropic Ratio, LR=exp(VDlusi) in analogy with the foregoing. Since VDlusi is <0 or =0, it is clear the exp(VDlusi)<1 or =1, since exp(0)=1. LR can never be greater than 1, since, physiologically, VDlusi can only be 0 in the case of perfect health, and less than 0 in the absence of perfect health.

If the patient's Heart Failure is purely Systolic (Inotropic), then VDlusi=0. If the patient's Heart Failure is purely Diastolic (Lusitropic), then VDino=0. It can be hypothesized that purely Systolic, or purely Diastolic Heart Failure does not really exist in Nature. Rather, it may be more likely that ALL cases of HF are on some level, 'mixed' Systolic and Diastolic. But one or the other may be very small, or negligible.

As alluded to elsewhere herein, we can describe the whole HF Picture using the Total Myocardial Function Fraction, TMFF={(VDino^2+VDlusi^2)^1/2}/(2^(1/2)). To calculate VDino or VDlusi, one must subtract the higher Intercept from the universal Intercept-Slope Tradeoff Function at a given Slope, from the lower Intercept that you get from the Calibration Curve of the individual patient whose condition you are trying to characterize and quantify. That is why VDino and VDLusi are negative numbers, and are equal to 0 only if the patient being assessed has a healthy myocardium.

Alternatively, let {VDino, VDlusi} be a 2-dimensional (x,y) vector space. And let (VDino, VDlusi) be a point in that space, that describes a particular patient with Heart Failure per the procedure described in the above.

Then (VDino, VDlusi) describes a Heart Failure Vector HF in {VDino, VDlusi} space, that clearly quantifies the character and magnitude of a particular patient's Heart Failure at a given point in time, in a clear and rigorous way.

Let the norm of the Vector HF be given by HF= (VDino^2+VDino^2)^1/2. HF gives us a metric of the magnitude of the patient's Total Heart Failure Disease. The vector HF makes an angle THETAhf with the x-axis, VDino such that tan(THETAhf)=VDlusi/VDino. (Recall that VDino is represented on the x-axis, and VDlusi is represented on the y-axis of {VDino VDlusi}.)

Moreover, if THEAThf is <45 degrees, then the patient's HF is said to be Systolic Predominant. And, if THETAhf is >45 degrees, then the patient's HF is said to be Diastolic Predominant If THETAhf=45 degrees, then the patient's HF is equal parts Systolic and Diastolic in character, at the time the measurement is made.

It is clear that the magnitude and the angle of the HF vector will change over the usual five year natural history of heart failure; something clinically useful can be learned from following its trajectory through {VDino, VDlusi} space over time. Truly by following it, one can see if, by his or her interventions and therapies, whether or not one has 'moved the needle' for the patient's benefit. This innovation would also be of interest to drug companies seeking to develop new money-saving solutions in this high-cost clinical space.

The forgoing would serve to put the taxonomy and quantification of Systolic and Diastolic HF on a firmer, clearer metrical footing than what is now the case in the present state of the art.

The preferred embodiment of the invention as disclosed herein utilizes the electromechanical system and certain methods disclosed in, the '665 patent, the '300 patent, and the '047 application, but it is important to understand that other system embodiments are intended to be covered hereby and that this application is not restricted to the preferred embodiment. Similarly, certain methods disclosed in the '665 patent, the '300 patent, or the '047 application, may be utilized in order to provide electronic signals that can be used to measure the vertical distance from the downward sloping line of the Universal Y-intercept vs. Slope plot (the Tradeoff Functions, as in FIGS. 1 and 2), based on the results of many individual calibration curves from healthy normal subjects, to the point (b,a)=(Slope, Intercept) that represents the individual calibration curve of the patient whose inotropic or lusitropic impairment is to be assessed.

To reiterate, the calibration curve is of the form ln(Strain Rate)=a+b/(E−M). (E−M) is either (E−M)ino in the Inotropic Function Case, or (E−M)lusi in the Lusitropic Function Case. The Strain Rates are likewise Inotropic with respect to 1/(E−M)ino, or Lusitropic, with respect to 1/(E−M)lusi. Only the magnitudes of the Strain Rates are used, since the ln(Strain Rate) is not defined if the argument of the function is <0, as it is, by convention, in the Inotropic case.

It should be noted that the instant disclosure is not intended to restrict the breadth of the invention described herein to any single embodiment or use. For example, and without limitation, in addition to the more immediate specific applications described herein, it is expected that other applications for solution to other heart related problems are covered hereby, such as for use in detecting the phonocardiogram or the seismocardiogram on morbidly obese people. The solution of that problem presently requires amplification and sophisticated digital filtering and signal processing. A different solution would be to implant an accelerometer under the skin closer to the rib cage. This would improve the signal to noise ratio. Yet another solution would be to do a transesophageal echocardiogram and dobutamine stress test under anesthesia. Other approximations to the Seismocardiogram, derived from millimeter wavelength radiofrequency currents that can easily penetrate the chest walls of morbidly obese patients and be reflected from the surface of the heart may serve as the basis of the timing and amplitude of the 'M' event in the (E−M) interval. Still another approach would be to use a precordial doppler ultrasound transducer whose output is sent to a frequency-to-voltage converter. The resulting waveform can also be used to get the timing and amplitude of the 'M' event in the (E−M) intervals in systole and in diastole. Both the radiofrequency and the ultrasound doppler approaches would serve to provide solutions to the problem of monitoring patients who suffer from morbid obesity. The both would still be 'wearable'. The tradeoff here is the need for larger batteries or alternative current sources, since both the radiofrequency and the doppler ultrasound approaches require a continuous source of the external energy directed at the patient's heart. Nevertheless, superb engineering, and clever signal processing, and amplification may obviate the need for these alternative approaches, and allow us to rely entirely upon the natural signals emanating from the human heart.

It is important to understand that Universal Intercept-Slope Tradeoff Functions describe a useful property of the linear fitting parameters, (Slope, Intercept) of a particular set of Inotropic or Lusitropic Calibration Curves. A Calibration Curve is a linear function that relates any exclusively mechanical cardiac performance metric, (such as the maximum (systolic) and minimum (diastolic) value of the first derivative of the Left Ventricular Pressure curve obtained by invasive catheterization, or the myocardial Strain Rate obtained from 2D transthoracic echocardiograph), to a non-invasively obtained electrical-mechanical metric, such as 1/(E−M)ino and 1/(E−M)lusi.

The exclusively mechanical performance data from cardiac systole or cardiac diastole is log-transformed using natural logarithms, and it is placed on the y-axis, and 1/(E−M)ino from cardiac systole or 1/(E−M)lusi from cardiac diastole is placed on the x-axis, then the relation between these two variables, one (y-axis) exclusively mechanical and the other (x-axis) uniquely electrical-mechanical, is a linear one. To be clear, Cardiac Systolic events and metrics are exclusively related to 1/(E−M)ino. Cardiac Diastolic Events are exclusively related to 1/(E−M)lusi. These linear relationships have two fitting parameters, (Slope, Intercept). A full description of this invention's teaching as to the creation of Inotropic and Lusitropic Calibration Curves is set forth in through hereinbelow.

Universal Intercept-Slope Tradeoff Functions are of two sorts, one for Inotropy during Cardiac Systole, and another for Lusitropy, during Cardiac Diastole. The Universal Inotropic Intercept-Slope-Tradeoff Function is comprised exclusively of (Slope, Intercept) data obtained during Cardiac Systole. And the Universal Lusitropic Intercept-Tradeoff Function is comprised exclusively of (Slope, Intercept) data obtained during Cardiac Diastole. There is no 'temporal mixing' of cardiac systolic and cardiac diastolic data. They are called 'Tradeoff Functions' simply because as the slope goes up, the intercept goes down, and vice-versa, according to a simple linear rule. A change in one of these quantities is effectively 'traded off' for an opposite change in the other.

These Universal Intercept-Slope Tradeoff Functions exclusively describe the behavior of hearts that are perfectly healthy and unburdened by any diseases, such as Myocardial Hypertrophy, Coronary Artery Disease, Heart Failure and Cardiomyopathy, or Valve Disease. These Universal Tradeoff Functions have a useful property; They can serve as a benchmark against which we can categorize, judge, and measure myocardial pathology. In particular, they can serve as a benchmark against which we can categorize, judge, and measure Heart Failure. This is regardless as to whether we are categorizing and measuring Inotropic Heart Failure with reduced Ejection Fraction, (HFrEF) or Lusitropic Heart Failure with preserved Ejection Fraction, (HFpEF). To be clear, a Universal Intropic Intercept-Slope Tradeoff-Function is comprised only of the fitting parameters (slope, Intercept) of the linear Inotropic Calibration Curves of many individuals who enjoy excellent cardiac health. Similarly, a Universal Lusitropic Intercept-Slope Tradeoff Function is comprised of the fitting parameters (slope, intercept) of the Lusitropic Calibration Curves of many individuals who enjoy excellent cardiac health. What is extraordinary about Universal Intercept-Slope Tradeoff Functions is that they obtain regardless of the age, gender, height, or weight of the subject, provided that the subject enjoys excellent cardiac health. Another way of saying this is, within practical limits, given cardiac health, the slope and intercept of the Universal Intercept-Slope Tradeoff Functions themselves, for both the Inotropic and Lusitropic case, are invariant with respect to age, gender, height, or weight of the subject.

The process by which a Universal Inotropic or Lusitropic Intercept-Slope Tradeoff Function is created follow very naturally from the forgoing definition:

Find N willing subjects who have good exercise tolerance and enjoy excellent cardiac health by any reasonable clinical standard or metric. N is sufficiently high such that meaningful statistics can be created, allowing for the calculation of Standard Errors of the Mean, and 95% Confidence Intervals. The N subjects also must be diverse in a way that includes age, height, weight, gender, and race. The goal is to create results that are a universal and useable approximation to the entire human race.

For each subject, measure the Inotropic Strain Rate in cardiac systole and the Lusitropic Strain rate in cardiac diastole.

Simultaneously measure the (E−M)ino and (E−M)lusi intervals in the systolic and diastolic parts of each cardiac cycle, respectively. See through for the details of how these time intervals are measured.

Now, have each subject perform exercise according to a clinically acceptable exercise protocol, such as the Bruce Protocol on a treadmill, or stepping up and down on a step at a rate determined by a metronome. Alternatively, a Dobutamine stress test can be performed, at several rates of drug infusion in mg/kg/min to create a series of graded hemodynamic steady-states, according to clinical protocol for such tests. Atropine can be given at the highest doses if the heart rate does not appreciably increase.

At each steady state of increased exercise or increased drug infusion rate, make simultaneous measurements of m consecutive heartbeats. 'in' is a number on the order of 10 consecutive heartbeats and is intended to allow the averaging of (E−M)ino and (E−M)lusi over of the respiratory variation in at least two consecutive breaths.

At each increase in exercise or drug infusion rate, make simultaneous measurements of Inotropic and Lusitropic Strain Rates, and also both of the (E−M)ino and (E−M)lusi time intervals that are characteristic of each increase in Inotropic and Lusitropic function that occur with each increase in exercise or drug infusion rate.

Now separate the Inotropic Strain Rates from the Lusitropic Strain Rates, and the (E−M)ino from (E−M)lusi intervals. Next, pair the Inotropic Strain Rates with the simultaneous (E−M)ino intervals, and the Lusitropic Strain Rates with the simultaneous (E−M)lusi intervals.

For each subject, this will create a series of m ordered pairs ((E−M)ino, (Inotropic Strain Rate)), and ((E−M)lusi, (Lusitropic Strain Rate)), at each hemodynamic steady-state, whether the hemodynamic steady-state is created by exercise or drug infusion.

Let there be i steady-state levels of inotropic and lusitropic function including one baseline level at rest, and four different levels of exercise or drug infusion rate. So, i is a small number, greater than 1 and on the order of 5.

For the ith exercise or drug infusion level, average all in consecutive values of (E−M)ino and separately, average all in consecutive values (E−M)lusi to get AVG(E−M)ino=SUM[(E−M)ino]/m and AVG(E−M)lusi=SUM[(E−M)lusi]/m Next, for each ith value of AVG(E−M)ino and AVG(E−M)lusi, calculate the reciprocals 1/(AVG(E−M)ino)i and 1(AVG(E−M)lusi)i This yields i pairs of averaged 1/(E−M)ino and 1/(E−M)lusi for each healthy subject. Each ith pair represents a different, stepwise increasing hemodynamic steady state.

Now, for each ith 1/(AVG(E−M)ino), pair it with the in simultaneous and consecutive inotropic strain rates measured with the 2D echocardiography that correspond to the same heartbeats that were used to measure 1/(E−M)ino.

Let AVG(Strain Rate)ino=SUM(Strain Rate)/m

Now take the natural logarithm of the ith average Strain Rate so that for the ith exercise level, ln(AVG(Strain Rate)ino)i=ln(SUM(Strain Rate)ino)/m)i Next, do the same for the in simultaneous and consecutive Lusitropic Strain Rates at the ith level of exercise, (ln(AVG(Strain Rate)lusi)i=ln(SUM(Strain Rate)lusi/m)i Now we have two sets of i ordered pairs of data, one for the Inotropic case, and one for the Lusitropic Case; {1/(AVG(E−M)ino)i, ln(AVG(Strain Rate)ino)i} and {(1(AVG(E−M)lusi)i), ln(AVG(Strain Rate)lusi)i}

We plot (1/AVG(E−M)ino)i on the x-axis and the (ln (AVG(Strain Rate)ino)i on the y-axis for each ith change in the hemodynamic steady state. This will generate the Inotropic Calibration Curve for this particular healthy individual, who is a member of a set of N such persons.

Lastly, we plot (1/AVG(E−M)lusi)i on the x-axis and (ln(AVG(Strain Rate)lusi)i on the y-axis for each ith change in the hemodynamic steady state. This will generate the Lusitropic Calibration Curve for this same particular healthy individual, who is a member of a set of N such persons.

We create an Inotropic Calibration Curve and a Lusitropic Calibration Curve for all N healthy subjects in our diverse sample. Initially, we will restrict membership in the set {N} exclusively to healthy adults. We can go on to study infants and children afterward, and we can speculate that as people grow from prematurity to infancy to adulthood, that there are developmental changes that occur with respect to Inotropy and Lusitropy and their relation to changes in (E−M) that can be assessed using these methods, which will need to be adjusted for developmental age, rather like a pediatrician's Height-Weight Growth Curve, with percentile stratifications as a function of chronological age from birth.

Each linear Calibration Curve has two fitting parameters, which we can write as an ordered pair, (Slope, Intercept). There will be N Inotropic Function Pairs, and N Lusitropic Function Pairs.

Now, plot the N Inotropic Function ordered pairs (Slope, Intercept) in (x,y) space. That is a Universal Inotropic Intercept-Slope Tradeoff Function.

Next, plot the remaining N Lusitropic Function ordered pairs (Slope, Intercept) in (x,y) space. That is a Universal Lusitropic Intercept-Slope Tradeoff Function.

On both of these Intercept-Slope Tradeoff Function x-axes, the units of Slope are ln(Strain rate)/(1/sec)=sec*ln (sec^-1).

On both of these Intercept-Slope Tradeoff Function y-axes, the units are ln(Strain Rate)=1n(sec^-1), since Strain, by itself, is a dimensionless quantity.

Both of these functions described in and will be downward sloping linear functions of the form Intercept=p−q (Slope). The constants(q,p)ino are the slope and intercept of the Universal Inotropic Intercept-Slope Tradeoff Function. The constants (q,p)lusi are the slope and intercept of the Universal Lusitropic Intercept-Slope Tradeoff Function. We posit that (q,p)ino and (q,p)lusi are discoverable, universal constants for all healthy humans, and that if N is a sufficiently high number, then meaningful and useful Standard Errors of the Mean, along with 95% Confidence Intervals can be calculated for them. In a sense, (q,p)ino and (q,p)lusi are Vitruvian constants of vigorous cardiac health, of a 'Cor sanum in corpore sano' that is, 'A sound heart in a sound body'. (See FIG. 1 and FIG. 2.)

We further posit that these Universal Intercept-Slope Tradeoff Functions can be used as benchmarks for myocardial health, and that when slopes and intercepts of the Calibration Curves of individual patients don't line up when mapped along with these universal functions, and there is daylight between the individual's point and the universal line, then that is an indication of functional myocardial pathology, either inotropic, or lusitropic or both. In premature infants, infants, and children that same deviation or 'daylight' may serve to accurately quantify an age-related degree of cardiac development toward normal adult function. Such deviation can be standardized as a function of birth age and used diagnostically by pediatric cardiologists to assess patients individually in the same way that general pediatricians use the growth chart.

Using this approach, myocardial pathology can be detected early in the natural history of heart failure, quantified, and monitored. Patients whose Intercept is lower by any amount that exceeds the 95% Confidence Interval around the value given by the Universal Intercept-Slope Tradeoff Function, but who are asymptomatic may be thought of as having Pre-HF. Reference to either the Inotropic or the Lusitropic Intercept-Slope Tradeoff Function will reveal which type—Inotropic or Lusitropic—Pre-HF is there.

As described above, the instant invention teaches the importance of the determination of the Electrical Events 'E' and the Mechanical Events 'M' in an Individual Research Subject's or an individual Patient's (E–M)ino and (E–M)lusi Electrical-Mechanical Intervals in Cardiac Systole and Cardiac Diastole, respectively In through above, it is disclosed how the (E–M)ino and (E–M)lusi time intervals are used to construct Calibration Curves for individual research subjects or individual patients. And we described how, starting with a set of N healthy individuals, the (Slope, Intercept) fitting parameters of those individual's Calibration Curves can be pooled to craft Universal Inotropic and Lusitropic Intercept-Slope Tradeoff Functions, and how they may be used by clinicians to evaluate individual patients.

The individual Inotropic Calibration Curve allows us to determine the natural log of the Myocardial Systolic Strain Rate given 1/(E–M)ino. A separate Lusitropic Calibration Curve allows us to determine the natural log of the Myocardial Diastolic Strain Rate given 1/(E–M)lusi. To obtain the actual Strain Rate from its natural log, all we need do is raise the base e of the natural log (approximately 2.718 . . . ) to a power equal to the natural log of the Strain Rate.

The reciprocals of the time between a signal electrical event and its concomitant signal mechanical event, 1/(E–M)ino and 1/(E–M)lusi, can be understood intuitively as a 'Speed of Electrical-Mechanical Transduction', and a 'Speed of Electro-Mechanical De-Transduction' for an average cardiomyocyte or a section of myocardial tissue. Each Calibration Curve makes a statement about the extent to which Myocardial Strain Rates are an exponential function of the 'Speed of Electrical-Mechanical Transduction' in the Inotropic case, or the 'Speed of Electrical-Mechanical De-Transduction' in the Lusitropic case.

We will now make explicit how (E–M)ino and (E–M)lusi are calculated. Their calculation follows intuitively from consideration of the Wiggers Diagram, referenced in the present patent application, which depicts the exquisite physiological choreography between the determinative electrical events in the ECG and their subsequent mechanical events. During Cardiac Systole, we see that the electrical QRS complex immediately precedes the rapid closure of the Mitral Valve and the report of the S1 heart sound in the phonocardiogram. In Cardiac Diastole, we see that the electrical T-wave rapidly follows the QRS complex, and that the initiation of the T-wave is rapidly followed by the closure of the Aortic Valve, and the subsequent S2 heart sound. The S1 and S2 heart sounds both also have well-defined and detectable event analogues in the Seismocardiogram.

The relationship between 'E' and 'M' in an (E–M) interval is that of an electrical antecedent to a causally related subsequent Mechanical event, in the same sense that lightning is antecedent to thunder. The Mechanical 'M' in an (E–M)ino or (E–M)lusi interval is not limited to events in a Phonocardiogram or Seismocardiogram. 'M' could be an event in an in a ventricular pressure wave, or its first (or higher) time derivative. 'M' could be an event in a peripheral arterial wave, or its time derivatives, at a given distance from the Aortic Valve. 'M' could be an event in a Doppler signal from a 1 MHz ultrasound transducer placed in an anatomically standardized location over the left ventricle, whose output is run through a frequency to voltage converter, or its time derivatives. 'M' could be millimeter wavelength radio signal reflected from the surface of the heart through the chest wall, whose Doppler shift is also passed through a frequency to voltage converter, or it's time derivatives. Similar Doppler measurements could be made with a near-infrared light emitting diode. The point is, 'M' is a signal event in ANY metric of mechanical heart wall motion or motion of the blood. These last three examples might be advantageously used to get useful signals from patients who are obese. The tradeoff is that these last three examples require an external source of power. Regardless of how exactly we measure 'M', the linear equations relating (E–M) to the natural log of said mechanical activity in Calibration Curves will still work. So will the linear equations of Intercept-Slope Tradeoff Functions continue to work. The only difference is that the values of the constants—the slopes and intercepts—will change in order to accommodate the different units of 'M'.

For (E–M)ino, the 'E' event can be the Q-wave of a single lead II ECG. Alternatively, the ECG can be differentiated twice with respect to time, which serves to amplify and invert the Q-wave, yielding the time of a Q"max event, in a way that causes the signal to rise usefully out of the noise (See FIG. 1). This Q-wave, or Q"max event is the 'tipping point' at which the myocardium has wholly and irreversibly 'committed' to depolarization and subsequent contraction. Using appropriate software, the time of this event is extracted from the real-time ECG data stream for each heartbeat. By 'Q-wave' or Q"max, we understand the time of a salient electrical event that is antecedent to a ventricular contraction.

The 'M' event, whose time is denoted by Mino, can be practically extracted from Phonocardiogram data in the time-neighborhood of the S1 sound that coincides with rapid closure of the Mitral Valve as the Left Ventricle rapidly and forcefully starts to contract. This is evident from inspection of the Wiggers Diagram referenced in the patent application. The S1 heart sound is a complex process of finite duration. In order to identify a precise moment in time that denotes M, it is useful to low pass filter the audio signal obtained from a stethoscope below a frequency on the order of 100 Hz. A large amplitude peak will manifest itself, which can serve as 'Mino'. Alternatively, the low-pass filtered Phonocardiogram can be differentiated with respect to time, which manifests a very large peak in the time-neighborhood of the closure of the Mitral Valve, whose time can serve as Mino.

The time of the peak of the first derivative is necessarily just prior to the peak in the undifferentiated Phonocardiogram signal.

Alternatively, or concurrently, it is possible to appreciate an event in the Seismocardiogram that occurs in the time-neighborhood of S1 in the Phonocardiogram. A peak in amplitude is clearly evident when the Seismocardiogram is Lowpass filtered below a frequency on the order of 100 Hz. The time of this peak may be used to represent Mino. The Lowpass filtered Seismocardiogram can be advantageously differentiated with respect to time. This results in several very sharply defined peaks in the rate of acceleration. The rate of change in acceleration per unit time is formally defined as 'Jerk', or dA/dt, which is usefully located in the time neighborhood of the closure of the Mitral Valve and can also serve as Mino. The time of the peak of the first derivative is necessarily just prior to the peak in the undifferentiated Seismocardiogram signal.

Given the foregoing, we can simply define (E−M)ino= (Mino-Q"max), since Mino will always occur after Q"max, and the timestamp Mino will always be larger than the timestamp Q"max. By definition, (E−M)ino>0.

For (E−M)lusi, the 'E' event requires that the ECG be differentiated twice with respect to time, which serves to amplify and invert the T-wave, with two obvious peaks on either side of the dip of the inverted T-wave. See FIG. 5. The initial (leftmost) second derivative peak just prior to the inverted T-wave dip marks the time of the T"max event, in a way that causes the signal to rise usefully out of the noise. This T"max event is the 'tipping point' at which the myocardium has wholly and irreversibly 'committed' to repolarization and subsequent relaxation of the tension that developed during systole. Using appropriate software, the time of this T"max event is extracted from the real-time ECG data stream for each heartbeat. By T"max, we understand the time of a salient electrical event that is antecedent to a ventricular relaxation.

The 'M' event in (E−M)lusi, whose time is denoted by Mlusi, can be practically extracted from Phonocardiogram data in the time-neighborhood of the S2 sound that coincides with the rapid closing of the Aortic Valve. Note that the Left Ventricle starts to relax from its peak and lose pressure just prior to the closing of the Aortic Valve. This is evident from inspection of the Wiggers Diagram referenced in the patent application. The S2 heart sound is a complex process of finite duration. In order to identify a precise moment in time that denotes Mlusi, it is useful to low pass filter the audio signal obtained from a stethoscope below a frequency on the order of 100 Hz. A large amplitude peak will manifest itself, which can serve as Mlusi. Alternatively, the low-pass filtered Phonocardiogram can be differentiated with respect to time, which manifests a very large peak in the time-neighborhood of the closure of the Aortic Valve, whose time can serve as Mlusi. The time of the peak of the first derivative is necessarily just prior to the peak in the undifferentiated Phonocardiogram signal. In our pilot study, we heuristically used the undifferentiated Phonocardiogram in the Lusitropic case.

Figure 5:
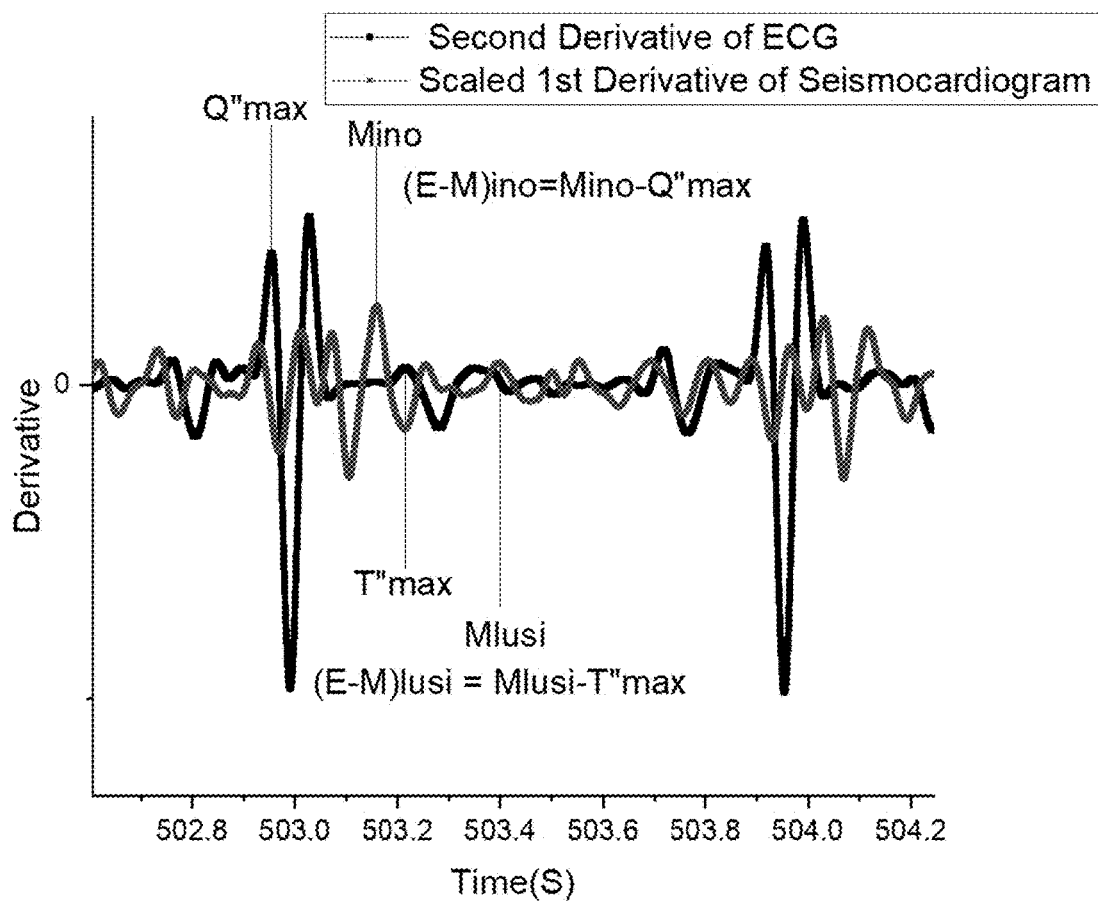
FIG. 5 is a cartesian coordinate mapping of a first derivative of a representative seismocardiogram and a second derivative of a representative electrocardiogram against time.

Alternatively, or concurrently, it is possible to appreciate an event in the Seismocardiogram that occurs in the time-neighborhood of S2 in the Phonocardiogram, as shown in FIG. 5. A peak in amplitude is clearly evident when the Seismocardiogram is Lowpass filtered below a frequency on the order of 15 Hz. See FIG. 5. The time of this peak may be used to represent Mlusi. The Lowpass filtered Seismocardiogram can be differentiated with respect to time. This results in several very sharply defined peaks in the rate of acceleration. The rate of change in acceleration per unit time is formally defined as 'Jerk', or dA/dt, where a peak is usefully located in the time neighborhood of the closure of the Aortic Valve and can serve as Mlusi. The units of 'Jerk' are meters/sec^3. In our pilot study, we heuristically used the undifferentiated Seismocardiogram in the Lusitropic Case.

Given the foregoing, we can simply define (E−M)lusi= (Mlusi-T"max), since Mlusi will always occur after T"max, and the timestamp Mlusi will always be larger than the timestamp T"max. By definition, (E−M)lusi>0

FIG. 5 shows an example of processed ECG"(t) overlayed over scaled SEISMO'(t) data with two QRS complexes. ECG"(t) is in black, and SEISMO'(t) in red. To the left at the top, Q"max and Mino are identified during Cardiac Systole. Time, in seconds, is shown on the x-axis. The times (Mino−Q"max)=(E−M)ino. The times T"max and Mlusi are shown following in time, during Cardiac Diastole. (Mlusi-T"max) =(E−M)lusi. In our pilot study, the $1^{st}$ derivative SEISMO'(t) was used to determine Mino, and the undifferentiated SEISMO(t) [not shown in this figure] was used, heuristically, to determine Mlusi.

As stated above, while it is the intention of this application to describe preferred embodiments of the instant invention, the present application should not to be read so as to preclude its coverage of similar embodiments of the system of the present invention that can be used to achieve the desired results of monitoring and patient care using the methods and the algorithms described herein.

What is claimed is:

1. A system for non-invasive detection and quantification of systolic and diastolic heart failure of a patient comprising:
    a non-invasive electronic heart function measurement device providing electronic outputs related to lusitropic and inotropic electrical cardiac activity;
    a non-invasive mechanical heart function measurement device providing mechanical outputs related to lusitropic and inotropic mechanical cardiac activity;
    a converting unit connected to said mechanical heart function measurement device for converting said mechanical outputs of said device into an electronic output related to said mechanical cardiac activity;
    a computer platform comprising a processing unit, an application program, memory means, and output means, said memory means storing a universal intercept-slope tradeoff function for inotropic function based on heart function of healthy patients and storing a universal intercept-slope tradeoff function for lusitropic function based on heart function of healthy patients;
    a connection from the output of said electronic heart function measurement device to the input of said processing unit;
    a connection from the output of said converting unit to the input of said processing unit,
    whereby said application program digitizes and processes said inputs to said processing unit in order to determine: (a) an inotropic electrical mechanical time interval for said patient's heart function and a lusitropic electrical mechanical time interval for said patient's heart function; and (b) an inotropic calibration curve of defined slope and intercept for said patient's heart function and a lusitropic calibration curve of defined slope and intercept for said patient's heart function; said application program comparing said inotropic calibration curve to said stored universal intercept-slope tradeoff function for inotropic function and said lusitropic calibration curve to said stored universal intercept-slope tradeoff function for lusitropic function in order make an assessment of myocardial well-being or myocardial pathology of said patient.

2. The system of claim 1 in which said assessment is detection and quantification of systolic heart failure.

3. The system of claim 2 in which said patient is not symptomatic.

4. The system of claim 1 in which said assessment is detection and quantification of diastolic heart failure.

5. The system of claim 4 in which said patient is not symptomatic.

6. A method for non-invasive detection and quantification of systolic and
diastolic heart failure of a patient comprised of the steps of
placing on the chest of a patient a non-invasive electronic heart function measurement device that provides a first electronic signal related to said patient's electrical cardiac activity including QRS complexes;
connecting said first electronic signal of such electronic heart measurement device to one input of a processing system having a memory;
storing in said memory of said processing system a universal intercept-slope tradeoff function for inotropic function based on heart function of healthy patients and a universal intercept-slope tradeoff function for lusitropic function based on heart function of healthy patients;
digitizing within said processing system said first electronic signal;
placing on the chest of said patient a non-invasive mechanical heart function measurement device that provides an output related to mechanical cardiac activity;
converting said output of said mechanical heart function measurement device into a second electronic signal;
connecting said converted second electronic signal to a second input of said processing system;
digitizing within said processing system said second electronic signal;
processing said digitized inputs to said processing system in order to determine an inotropic electrical mechanical time interval for said patient's heart; processing said digitized inputs to said processing system in order to determine a lusitropic electrical mechanical time interval for said patient's heart; using said inotropic interval and simultaneous inotropic myocardial strain rate data obtained from a non-invasive electronic heart function measurement device to determine an inotropic calibration curve of defined intercept and slope at rest and over varying degrees of exercise for said patient's heart;
using said lusitropic interval and simultaneous lusitropic myocardial strain rate data obtained from a non-invasive electronic heart function measurement device to determine a lusitropic calibration curve of defined intercept and slope at rest and over varying degrees of exercise for said patient's heart;
comparing said intercept and slope of said inotropic calibration curve to said stored universal intercept-slope tradeoff function for inotropic function;
comparing said intercept and slope of said lusitropic calibration curve to said stored universal intercept-slope tradeoff function for lusitropic function;
making an assessment of myocardial well-being or myocardial pathology of said patient using the results of said comparing of inotropic functions and said comparing of lusitropic functions.

7. The method of claim 6 in which said assessment is detection and quantification of systolic heart failure.

8. The method of claim 7 in which said patient is not symptomatic.

9. The method of claim 6 in which said assessment is detection and quantification of diastolic heart failure.

10. The method of claim 9 in which said patient is not symptomatic.

11. A method for determining a universal intercept-slope tradeoff function for inotropic function comprising the steps of:
selecting a number of heart healthy patients of diverse height, weight, age, and gender;
measuring for each said healthy patient using a non-invasive electronic heart function measurement device intropic strain rate and inotropic electrical mechanical interval at rest and over a range of exercise according to an exercise protocol, or a catecholamine drug infusion protocol, to achieve a series of intropic steady-states of varying degrees of inotropy;
plotting the natural logarithm of the absolute value of the inotropic strain rate against the reciprocal of said electrical-mechanical interval at rest and at each inotropic steady-state; with the result that said steady states appear as points in a linear function in $\{1/(E-M)ino, \ln(abs(\text{Inotropic Strain Rate}))\}$ space, with a well-defined slope and intercept for slope >0, said function being defined as said patient's inotropic calibration curve;
writing fitting parameters for said linear function as (Slope, Intercept) as (x,y) points in {Slope, Intercept} space;
graphing (Slope, Intercept) of each of said patients in {Slope, Intercept} space, as a downward sloping linear function, with resulting universal inotropic fitting parameters slope and intercept being graphed as a universal inotropic intercept-slope tradeoff function,
whereby any deviation from said function for an individual being evaluated for heart disease being an indication of inotropic heart failure.

12. A method for determining a universal intercept-slope tradeoff function for lusitropic function comprising the steps of:
selecting a number of heart healthy patients of diverse height, weight, age, and gender;
measuring for each said healthy patient using a non-invasive electronic heart function measurement device lusitropic strain rate and lusitropic electrical mechanical interval at rest and over a range of exercise according to an exercise protocol, or a catecholamine drug infusion protocol, to achieve a series of lusitropic steady-states of varying degrees of lusitropy;
plotting the natural logarithm of the absolute value of the lusitropic strain rate against the reciprocal of said electrical-mechanical interval at rest and at each lusitropic steady-state; with the result that said steady states appear as points in a linear function in $\{1/(E-M)ino, \ln(abs(\text{lusitropic Strain Rate}))\}$ space, with a well-defined slope and intercept for slope >0, said function being defined as said patient's lusitropic calibration curve;
writing fitting parameters for said linear function as (Slope, Intercept) as (x,y) points in {Slope, Intercept} space;
graphing (Slope, Intercept) of each of said patients in {Slope, Intercept} space, as a downward sloping linear function, with resulting universal lusitropic fitting parameters slope and intercept being graphed as a universal lusitropic intercept-slope tradeoff function, whereby any deviation from said function for an individual being evaluated for heart disease being an indication of lusitropic heart failure.

13. A non-transitory computer readable medium storing the universal tradeoff function for inotropic function.

14. A non-transitory computer readable medium storing the universal tradeoff function for lusitropic function.

* * * * *